United States Patent [19]

Turner

[11] Patent Number: 5,101,970
[45] Date of Patent: Apr. 7, 1992

[54] PERSONAL IDENTIFICATION SYSTEM

[76] Inventor: Mike L. Turner, 3834 Poplar Springs Rd., Gainesville, Ga. 30501

[21] Appl. No.: 580,094

[22] Filed: Sep. 10, 1990

[51] Int. Cl.[5] .................. B65D 43/16; A01N 1/00
[52] U.S. Cl. ............................. 206/223; 53/440; 53/449; 206/803
[58] Field of Search ............. 206/223, 570, 571, 572, 206/438, 803, 459, 232; 53/440, 449

[56] References Cited

U.S. PATENT DOCUMENTS

| | | | |
|---|---|---|---|
| 2,655,152 | 10/1953 | Turner et al. | 206/438 |
| 3,255,871 | 6/1966 | Butler | 206/438 |
| 3,911,918 | 10/1975 | Turner | 206/438 |
| 4,472,357 | 9/1984 | Levy et al. | 206/459 |

FOREIGN PATENT DOCUMENTS 0054221 6/1982 European Pat. Off. ............ 206/438

*Primary Examiner*—Jimmy G. Foster
*Attorney, Agent, or Firm*—Hopkins & Thomas

[57] ABSTRACT

The present invention is a system for in-home collection and preservation of information for identifying and locating lost or missing loved ones. The system includes devices for collecting, sealing, and preserving hair, blood, and fingerprint samples from each loved one and for recording vital person data regarding each loved one. The information and samples are collected, sealed and stored in the family freezer to insure that the collected specimens remain viable indica of identification for long subsequent periods of time.

15 Claims, 1 Drawing Sheet

PERSONAL IDENTIFICATION SYSTEM

TECHNICAL FIELD

This invention relates to personal identification and particularly to a system for in-home collection and preservation of information for identification in the event of a missing or lost loved one.

BACKGROUND OF THE INVENTION

It has long been common to collect and preserve identifying information on virtually everything of value for insurance purposes in the event of theft or natural disaster. Curiously, however, identifying information about our most valuable assets, namely our loved ones, is seldom collected and preserved for use in the event a family member is abducted or otherwise becomes missing. This is indeed unfortunate since such information, if available, can be the critical link to evidence that could help identify, locate and possibly save the life of a missing loved one. Hair sample comparison and DNA print matching, for example, might be used by forensic pathologists to identify an unknown hair, blood, or tissue sample as that of a missing person, thereby generating a lead to locating such person. Furthermore, the simple recording of data such as a recent photograph, hair color, eye color, identifying marks, etc. can be invaluable in locating a missing child, for example, since such information can be quickly and widely disseminated among the public.

Tragically, some missing persons are victimized and killed by their abductors who often leave their victim's body in an isolated or inaccessible location. When such bodies are eventually found, they are often so deteriorated that identification through traditional means is impossible. In these instances, techniques such as DNA print matching can still provide a positive identification since every cell in an individual's body, even the cells of deteriorated remains, contains DNA cells having gene patterns that are unique to that individual alone. Sadly, however, DNA analysis is seldom fruitful in this regard because cell bearing specimens from only a minute fraction of missing persons are available for comparison to those of unidentified remains. As a consequence, many remains are never identified and, in fact, government agencies estimate that as many as 2000 unidentified bodies are buried each year in the U.S. alone. In the mean time, the families of these unidentified people will continue to grieve, not knowing whether their loved one is alive or dead.

A continuing and heretofore unaddressed need exists, therefore, for a system of collecting and preserving vital identifying information about and cell bearing specimens from family members and loved ones for use in the event a loved one becomes missing. Such a system should be complete, convenient, easy to use in the home without medical supervision and should be adapted to preserve cell bearing specimens such as blood for long periods without significant deterioration of the specimens. It is to the provision of such a system that the present invention is primarily directed.

SUMMARY OF THE INVENTION

The present invention comprises an in-home system for collecting and preserving a complete identification record of loved ones for use in the unfortunate event a loved one becomes missing. The system embodies the process of collecting and recording various information regarding loved ones, including fingerprints, vital information, hair samples, and blood samples; sealing the collected samples and information against deterioration and freezing at least the cell bearing specimens to insure the longevity and integrity thereof.

The system further comprises an identification kit for implementing the method of the invention. The kit includes devices for collecting and recording vital data and DNA bearing specimens and sealing the information and specimens in a container for storage in a home freezer. In use, vital data, fingerprints, blood samples, and hair samples are collected from each loved one, sealed, and placed in a home freezer for preservation. Should a loved one become missing, the preserved data for that person can be delivered to law enforcement agencies for use in locating and identifying the missing loved one.

It is thus an object of this invention to provide a convenient, easy to use, and inexpensive system for collecting and preserving a complete identification record of loved ones.

Another object of the invention is to provide a system for assisting law enforcement agencies in locating and identifying missing persons.

A further object of the invention is to provide loved ones with the peace of mind in knowing that should one of them become missing, a complete record for use in location and identification is readily available.

These and other objects, features, and advantages of the invention will become more apparent upon review of the following detailed description when taken in conjunction with the accompanying drawings.

DETAILED DESCRIPTION OF THE PREFERRED EMBODIMENT

Figure 1:
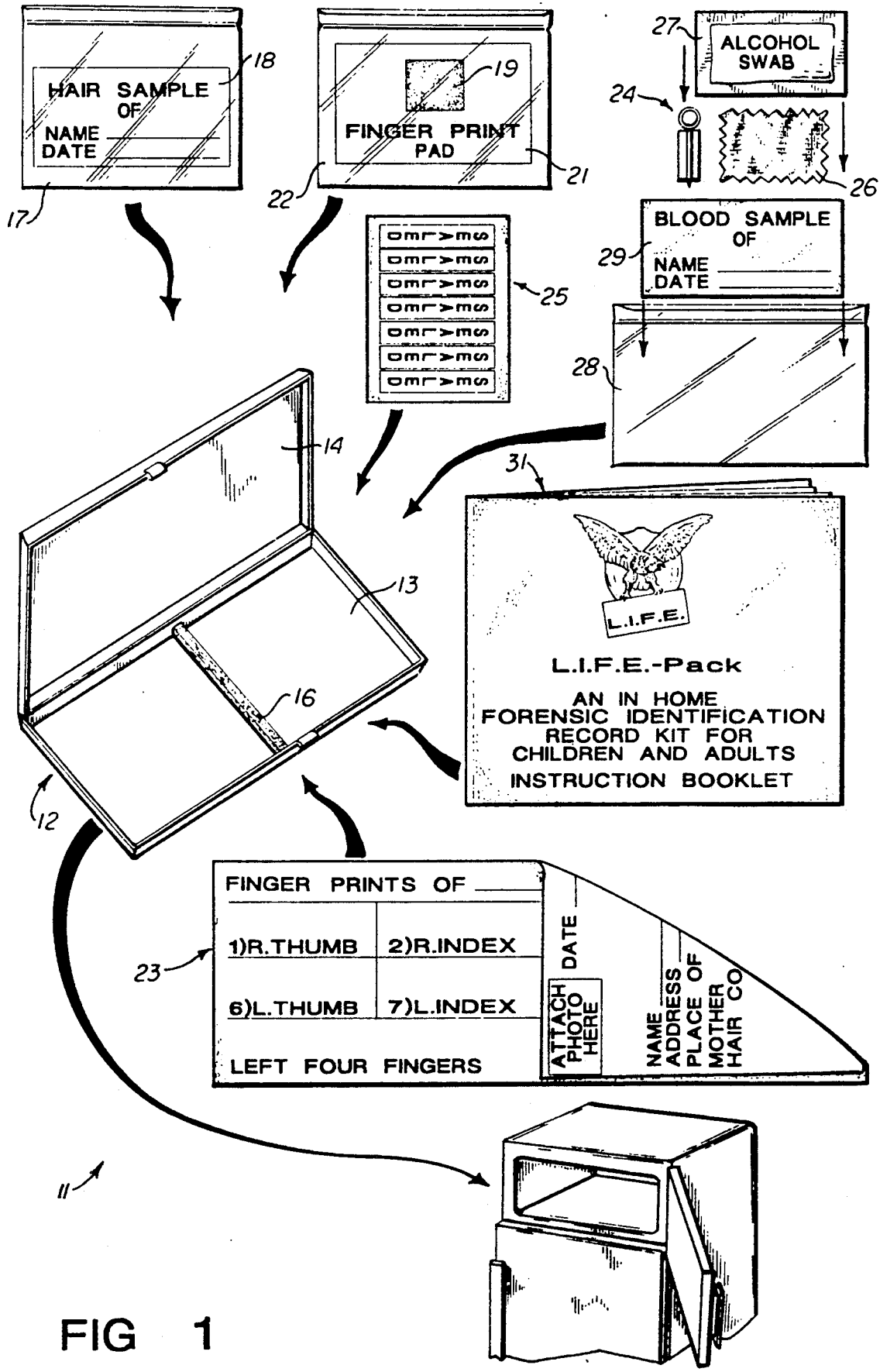
FIG. 1 is a perspective partially exploded view of a personal identification system that embodies principles of the invention in a preferred form.

Referring now in more detail to the drawing, in which reference numerals refer to salient elements of the preferred embodiment, FIG. 1 illustrates an identification system 11 that embodies principles of the invention in a preferred form. The system 11 includes a case 12 that is preferably formed of clear plastic and that includes a base member 13 having a hinged lid 14. A partition 16 is positioned within the base member 13 and subdivides it into two distinct storage areas.

The system is provided with a number of devices for collecting and preserving data and physical evidence from an individual for identification. More specifically, means for collecting and storing a sample of an individual's hair includes a sealable plastic envelope 17 adapted to receive the hair sample and to receive a card 18 bearing the date of the sample and the identity of the person from whom the sample was taken.

Means for capturing and preserving the fingerprints of the individual includes a fingerprint pad 19 that is impregnated with fingerprint ink and secured to a support card 21. The pad and card are in turn enclosed within a sealable plastic envelope 22 to prevent the pad from drying out prior to use. An identification card 23 has printed on one side a matrix for receiving the fingerprints of an individual in the usual way. The array includes positions for fingerprints of each finger of each hand as well as positions for prints of several fingers taken in conjunction. Space for providing the identity of the person whose fingerprints appear on the card is also provided.

Means for collecting and securing a sample of an individual's blood for use in DNA print identification includes a lancing tool 24 for piercing the tip of a finger to draw blood, a cloth patch 26 for receiving and securing a sample of the blood, and a sterile swab 27 for wiping the pricked finger before and after the blood sample has been taken. A sealable plastic envelope 28 is sized to receive and seal the patch 26 and blood sample thereon and a card 29 is provided for identifying the date of the sample and the person whose blood is contained within the patch 26.

Printed on the side of card 23 opposite the fingerprint matrix is a form for recording vital personal data regarding the individual whose identity is being secured. This form includes positions for recording the image of the individual through a photograph as well as other vital data such as name, address, place of birth, date of birth, hair color, eye color, etc. Such data can be and often is valuable in identifying persons who are alive but who may have lost their memories, grown older or disguised their identity.

Also included with the system is a booklet 31 that contains vital information regarding modern methods used in identifying individuals and that includes detailed instructions for use of the system of the present invention to secure the identities of loved ones. A set of decals 25 each imprinted with the word "SEALED" are provided for securing the collected data and specimens as detailed below.

USE OF THE SYSTEM

Use of the system of this invention to collect and preserve vital data about and physical specimens from loved ones is simple and easily carried out in the home. First, a photograph of each loved one is secured and attached to the corresponding identification card 23. All of the information solicited on the card is then entered in the spaces provided on the card.

The card 23 can then be turned over such that its fingerprint matrix faces up for recording fingerprints. In this regard, the fingerprint pad 19 and its support card 21 are removed from their sealed envelope 22. Each finger of the person being identified is then rolled slowly across the inked pad to deposit the fingerprint ink onto the fingertips. The fingers are then rolled in sequence across the card 23 in the positions of the matrix corresponding to each finger. Prints of the four fingers of the left and right hands are taken simultaneously and applied to their proper positions within the fingerprint matrix. The identification and fingerprint card 23 is thus completed and the fingerprint pad and its sealed envelope can be discarded if desired.

Next, a sample of the individual's hair is taken and prepared for preservation. Preferably, several hairs are cut from the individual's head and secured to the back of the card 18 with a staple or tape. The sample is then set aside to air dry for approximately one hour such that oil and other fluids can evaporate from the sample. This drying time is important because fluids contained within freshly cut hair samples can accelerate the deterioration of the samples if they are sealed along with the samples. Once the hair sample has dried for the specified time, the identification of the individual from whom the sample was taken and the date it was taken are provided on the card and the card and its attached sample are secured and sealed within the plastic envelope 17.

Finally, a sample of the individual's blood is collected and prepared for preservation. In this regard, the cloth patch 26, lancing tool 24, and sterile swab 27 are obtained and the end of the lancing tool is twisted off to reveal its blade. A fingertip of the individual being identified is then wiped with the swab and pierced quickly with the lancing tool to draw a small amount of blood from the finger. The patch 26 is applied to the fingertip to absorb the blood for preservation. The blood impregnated patch is then set aside for approximately one hour to allow unwanted fluids to evaporate from the blood sample. As with the hair sample, these fluids can accelerate the deterioration of the blood if sealed therewith such that the drying process is important for maximum longevity of the sample. The identification of the individual whose blood sample has been taken and the date the sample was taken are then provided on the card 29 and the card and blood impregnated patch 26 are secured and sealed within the plastic envelope 28.

With the hair and blood sample thus taken, dried and sealed within their envelopes, one of the adhesive decals 25 can be secured over the top edge of each envelope to insure that the contents of the envelopes are not subsequently tampered with or altered. The sealed and secured bags containing the hair and blood samples and the card 23 containing the fingerprints and vital data are then placed within the case 12 for storage. Preferably, data and samples for a number of loved ones, four for example, can be taken in the above described manner and placed within a single case 12. With the data and samples thus placed, the case 12 is closed by hinging its lid 14 shut over its base 13. A final one of the adhesive decals 25 can then be secured across a closed edge of the case to insure against tampering.

With the vital identifying information of all loved ones secured and sealed within their respective envelopes and within the case, the entire case can be placed within the family freezer for storage. In the freezer, the blood and hair samples are chilled to a temperature below their freezing point such that the useful life of these samples is extended long beyond that which they would exhibit under normal temperature conditions. Further, the low temperature within the freezer tends to enhance the longevity of the fingerprints and slows the aging and deterioration of photographs and other identifying information. Typically, specimens stored within the freezer can be expected to last and be usable for identification for a number of years whereas specimens stored at normal room temperatures may only last for a few weeks. It is therefore important that the specimens be stored within the freezer to insure their viability should they ever be needed to identify a missing loved one.

The invention has been described above in terms of a preferred embodiment. It will be obvious, however, that many variations of the illustrated embodiment might well be contemplated by ordinarily skilled artisans. The order in which information and samples are taken and sealed can, for example, be different than that illustrated above. Further, various means for sealing the hair and blood samples could also be used with results comparable to that of the sealable plastic envelopes of the preferred embodiment. Also, other types of sample such as, for example, skin tissue samples, could also be used with the illustrated system to provide specimens for DNA print analysis. These and other modifications, deletions and additions might well be made to the illustrated embodiment without departing from the spirit and scope of the invention as set forth in the claims.

I claim:

1. A method of assimilating and preserving information for use in subsequent identification of an individual with said method comprising the steps of:
   (a) collecting and recording identifying data about the individual;
   (b) collecting at least one specimen containing cells of the individual;
   (c) sealing the collected specimens against exposure to ambiance;
   (d) placing the recorded data and sealed specimen together for storage in distinct storage areas in a common storage container; and
   (e) chilling at least the collected specimen to a predetermined temperature sufficient to retard temporal deterioration of the specimen.

2. The method of claim 1 and wherein step (a) includes printing the identifying data on a card.

3. The method of claim 1 and wherein step (b) includes collecting a sample of the individual's blood.

4. The method of claim 1 and wherein step (c) includes depositing the collected specimen in a sealable envelope and sealing the envelope.

5. The method of claim 1 and wherein step (e) includes depositing the storage container containing the recorded data and sealed specimen in an in-home freezer.

6. A method of assimilating and preserving information for use in subsequent identification of an individual with said method comprising the steps of:
   (a) collecting and recording identifying data about the individual and printing the identifying data on a card;
   (b) collecting at least one specimen containing cells of the individual;
   (c) sealing the collected specimen against exposure to ambiance;
   (d) placing the recorded data and sealed specimen together for storage in distinct storage areas in a common storage container;
   (e) chilling at least the collected specimen to a predetermined temperature sufficient to retard temporal deterioration of the specimen; and
   wherein step (a) further includes affixing a photograph of the individual to the card.

7. A method of assimilating and preserving information for use in subsequent identification of an individual with said method comprising the steps of;
   (a) collecting and recording identifying data about the individual;
   (b) collecting at least one specimen containing cells of the individual;
   (c) sealing the collected specimen against exposure to ambiance;
   (d) placing the recorded data and sealed specimen together for storage in distinct storage areas in a common storage container;
   (e) chilling at least the collected specimen to a predetermined temperature sufficient to retard temporal deterioration of the specimen; and
   wherein step (b) includes collecting a sample of the individual's hair.

8. The method of claim 7 and further including the step of drying the collected hair sample prior to sealing it against exposure to ambience.

9. A method of assimilating and preserving information for use in subsequent identification of an individual with said method comprising the steps of:
   (a) collecting and recording identifying data about the individual;
   (b) collecting at least one specimen containing cells of the individual, including collecting a sample of the individual's blood;
   (c) sealing the collected specimen against exposure to ambiance;
   (d) placing the recorded data and sealed specimen together for storage and in distinct storage areas in a common storage container;
   (e) chilling at least the collected specimen to a predetermined temperature sufficient to retard temporal deterioration of the specimen; and
   wherein the step of collecting a sample of the individual's blood includes pricking the individual's fingertips to draw blood therefrom and depositing the blood on a cloth patch for preservation.

10. The method of claim 9 and further including the step of drying the collected blood sample prior to sealing it against exposure to ambience.

11. A method of assimilating and preserving information for use in subsequent identification of an individual with said method comprising the steps of:
    (a) collecting and recording identifying data about the individual;
    (b) collecting at least one specimen containing cells of the individual;
    (c) sealing the collected specimens against exposure to ambiance;
    (d) placing the recorded data and sealed specimens together for storage in distinct storage areas in a common storage container;
    (e) chilling at least the collected specimen to a predetermined temperature sufficient to retard temporal deterioration of the specimen; and
    wherein step (a) includes securing fingerprints of the individual.

12. A method of assimilating and preserving information for use in subsequent identification of an individual with said method comprising the steps of:
    (a) collecting and recording identifying data about the individual with said data including at least fingerprints of the individual;
    (b) collecting a specimen of the individual's hair and drying the collected hair specimen;
    (c) collecting a specimen of the individual's blood and drying the collected blood specimen;
    (d) sealing the collected hair and blood specimens against exposure to ambience;
    (e) placing the recorded identifying data together with the collected and sealed hair and blood specimens in a common storage container; and
    (f) depositing the storage container bearing the data and specimens in a freezer unit for retarding temporal deterioration of the samples.

13. The kit of claim 15 wherein said sealing means includes at least one sealable plastic envelope configured to receive and seal off the collected specimen.

14. The kit of claim 15 wherein said refrigeration means comprises a freezer unit.

15. A kit for use in assimilating information for use in subsequent identification of an individual, with said kit comprising:

a clear plastic case having a base member and a hinged lid, a partition means positioned within said base member which subdivides the base member into distinct storage areas;

a sealable means for collecting and containing a person's hair, said means being received in one of said storage areas;

means for capturing and preserving fingerprints of said individual, being received within a second sealable means, said second means and said capturing and preserving means being received in one of said storage areas; and means for collecting and securing a sample of a persons blood, said collecting and securing means being received in one of said storage areas.

* * * * *